United States Patent [19]

Lagerweij et al.

[11] Patent Number: 5,196,608
[45] Date of Patent: Mar. 23, 1993

[54] USE OF AN ALLYLCHLORIDE FOR PREPARING AN ALDEHYDE

[75] Inventors: Gerrit J. Lagerweij; Cornelis Bakker; Monique E. A. De Bruin-Van Der Flier, all of Weesp, Netherlands

[73] Assignee: Duphar International Research B.V., Weesp, Netherlands

[21] Appl. No.: 801,654

[22] Filed: Dec. 2, 1991

[30] Foreign Application Priority Data

Dec. 5, 1990 [EP] European Pat. Off. ........ 90203204.4

[51] Int. Cl.$^5$ .................... C07C 45/37; C07C 45/32
[52] U.S. Cl. .................................. 568/471; 568/465; 568/470; 568/476; 568/485; 568/488; 568/490
[58] Field of Search .............. 568/465, 490, 471, 476, 568/470; 468/485, 488

[56] References Cited

U.S. PATENT DOCUMENTS 4,745,229  5/1988  Otera et al. ...................... 568/490

FOREIGN PATENT DOCUMENTS

| 517127 | 10/1955 | Canada ............................ 568/471 |
| 0275892 | 7/1988 | European Pat. Off. .......... 568/471 |
| 2902805 | 7/1980 | Fed. Rep. of Germany . |
| 0011936 | 1/1982 | Japan ................................ 568/471 |
| 795227 | 5/1958 | United Kingdom ............. 568/490 |

OTHER PUBLICATIONS

Chemical Abstracts, vol. 113, No. 5, (Jul. 30, 1990), p. 548 Abstract No. 39943m.
Bulletin of the Chemical Society of Japan, vol. 63, No. 5, (May 1990), pp. 1328–1334; Sato et al; "Highly Stereoselect . . . ".
Agricultural and Biological Chemistry, vol. 52, No. 4, (Apr. 1988), pp. 989–996; Iriye et al; "Synthesis of Aliphatic . . . ".

Primary Examiner—Werren B. Lone
Attorney, Agent, or Firm—Stevens, Davis, Miller & Mosher

[57] ABSTRACT

The present invention relates to the use of an allylchloride of the general formula

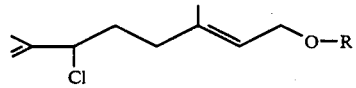

wherein R is a $C_1$–$C_{12}$ alkyl group or a $C_2$–$C_{12}$ alkenyl group, which groups may be substituted with one or more substitutents selected from the group consisting of $C_1$–$C_4$ alkoxy, halogen, unsubstituted phenyl and substituted phenyl; a (trihydrocarbyl)silyl group; a (dihydrocarbyl) (hydrocarbyloxy)silyl group; or a dihydropyran-2-yl group, a tetrahydropyran-2-yl group, a dihydrofur-2-yl group or a tetrahydrofur-2-yl group, which groups may be substituted with $C_1$–$C_6$ alkyl;

for preparing an aldehyde compound via an intermediate alcohol compound.

The invention further relates to a new allylchloride.

3 Claims, No Drawings

USE OF AN ALLYLCHLORIDE FOR PREPARING AN ALDEHYDE

The invention relates to the use of an allylchloride for preparing an aldehyde compound via an intermediate alcohol compound. The invention also relates to a new allylchloride and to its preparation.

Certain allylchlorides can be used as intermediates in processes for producing vitamin A. For example, 6-chloro-3,7-dimethyl-2,7-octadienyl acetate and its preparation from geranylacetate are disclosed in European patent applications 34496 and 282914, as well as in a publication by Suzuki et al in Bull. Chem. Soc. Jpn., 59, 1986, 3287-3288. This secondary allyl chloride can be converted to a primary allyl alcohol by a reaction with sodium formate to yield a primary allyl ester, followed by a selective saponification of the formate ester while leaving the acetate ester intact. Said selective saponification is performed by a transesterification of the allyl ester with the aid of sodium carbonate in methanol. These reactions are described in Japanese patent applications 63/227546, 63/227548 and 02/03-6148. As also described in said last-mentioned Japanese patent publication, the primary allyl alcohol thus obtained can be subjected to air oxidation to yield 8-acetoxy-2,6-dimethyl-2,6-octadien-1-al, which is a starting compound or synthon for the production of vitamin A according to the process as described e.g. by Otera et al in European patent application 187259 and in J. Org. Chem. 51, 1986, 3830-3833, 3834-3438.

The selective saponification to yield the desired allyl alcohol, as described in the above Japanese patent application 02/036148, is a serious disadvantage, because of the considerable risk of unintentional saponification of the acetate ester. To avoid this risk as far as possible, one has to resort to the use of sodium formate instead of e.g. sodium acetate in the conversion of the starting allylchloride, and to the use of alcohols such as methanol as a solvent. Moreover, the yield of the primary allyl alcohol after the saponification reaction is still unsatisfactory.

It is the object of the present invention to avoid the above disadvantage in the synthesis of a suitable aldehyde that can be used as a synthon in a convenient process of producing vitamin A or its esters.

This object can be achieved by using as a key intermediate in the synthesis of such an aldehyde an allylchloride, which according to the present invention is presented by the general formula

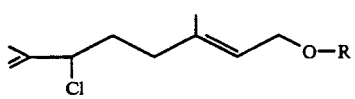

(I)

wherein
R is a $C_1-C_{12}$ alkyl group or a $C_2-C_{12}$ alkenyl group, which groups may be substituted with one or more substituents selected from the group consisting of $C_1-C_4$ alkoxy, halogen, unsubstituted phenyl and substituted phenyl; a (trihydrocarbyl)silyl group; a (dihydrocarbyl)(hydrocarbyloxy)silyl group; or a dihydropyran-2-yl group, a tetrahydropyran-2-yl group, a dihydrofur-2-yl group or a tetrahydrofur-2-yl group, which groups may be substituted with $C_1-C_6$ alkyl.

The above allylchloride can be used for preparing an aldehyde compound of the general formula

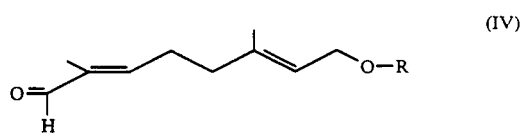

(IV)

wherein R has the above meaning, by successively:

(i) converting said allylchloride into an alcohol compound of the general formula

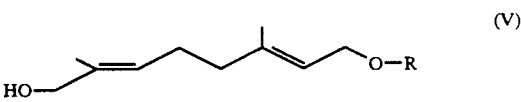

(V)

and (ii) oxidizing the alcohol compound thus obtained.

In the above meanings of R the term hydrocarbyl includes $C_1-C_8$ alkyl, $C_2-C_8$ alkenyl, $C_2-C_8$ alkynyl, phenyl and substituted phenyl. It will be obvious that such alkyl, alkenyl and alkynyl groups encompass both straight and branched groups. Suitable substituents of the phenyl group include $C_1-C_6$ alkyl, $C_1-C_6$ alkoxy and halogen; preferably three substituents at most are present on said phenyl group.

It has been found, that the above-defined allylchloride is excellently suitable in synthesizing an appropriate aldehyde that can be used as a synthon in a convenient process of producing vitamin A or its esters. Such a process is the subject of the non-prepublished European patent application 90200863.0. The aldehyde described therein and having the general formula

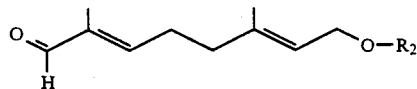

wherein $R_2$ has the meaning as defined in said patent application, can be obtained from the corresponding alcohol ($R_2=H$) by a reaction with a suitable $R_2$-introducing agent. Alternatively said aldehyde can be obtained by a notoriously toxic seleniumdioxide oxidation from the corresponding geranyl ether having the general formula

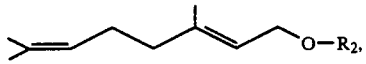

as described for related compounds in Tetrahedron Letters 1973, 281 and in J.Am.Chem.Soc. 99, 1977, 5526.

It is the merit of the present invention, however, that the use of the above allylchloride makes the above aldehyde, to be used as a synthon in the process of producing vitamin A, better accessible, thereby avoiding the disadvantages observed in the known process, described hereinbefore.

Preferably the allylchloride, to be used as a key intermediate in the synthesis of the above aldehyde, is characterized by the general formula

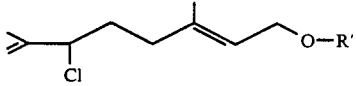

(II)

wherein

R' is a tert.($C_4$-$C_{12}$)alkylgroup, a tetrahydropyran-2-yl group, a tetrahydrofur-2-yl group, an ethoxyethyl group, or a tri(hydrocarbyl)silyl group wherein hydrocarbyl is selected from the group consisting of $C_1$-$C_8$ alkyl and phenyl.

Some allylchlorides to be used for the method of the present invention are known. Sato et al (Bull. Chem. Soc. Jpn.,63, 1990, 1328-1334) have described the above allylchloride of formula I, wherein R is a benzyl group. They have used this compound as an intermediate in the stereoselective synthesis of certain olefinic diols. The corresponding tetrahydropyranyl ether is described by Iriye et al in Agric. Biol. Chem., 52 (4), 1988, 989-996. This compound can be used as an intermediate in the preparation of certain unsaturated carbonyl compounds.

Various allylchlorides to be used for the method of the invention, however, are new. Therefore, the present invention also relates to a new allylchloride having the general formula

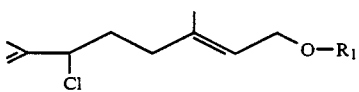

(VI)

wherein $R_1$ is a (trihydrocarbyl)silyl group or a (dihydrocarbyl)(hydrocarbyloxy)silyl group.

The term hydrocarbyl has been further defined hereinbefore.

More in particular the above new allylchloride of the present invention has the general formula

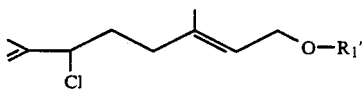

(VII)

wherein $R_1'$ is a (trihydrocarbyl)silyl group, wherein hydrocarbyl is selected from the group consisting of $C_1$-$C_8$ alkyl and phenyl.

Suitable examples of new allylchlorides are presented in the Examples.

The new allylchloride of the above general formula VI can easily be prepared by a chlorination of a geranyl compound of the general formula

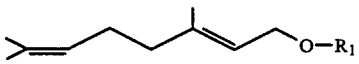

(III)

wherein $R_1$ has the above meaning.

Said chlorination is preferably carried out with the aid of a hypochlorite, preferably an aqueous solution of an alkalimetal hypochlorite such as sodium hypochlorite, in a two-phase system with an inert organic solvent, e.g. dichloromethane, at a temperature preferably slightly below room temperature. Other chlorinating agents such as trichloroisocyanuric acid can also be used. Such a chlorination of a related geranyl compound, viz. geranyl acetate, is described in the above European patent application 234496 and in the above Japanese patent application 02/036148.

The allylchloride can be converted into an ester of the general formula

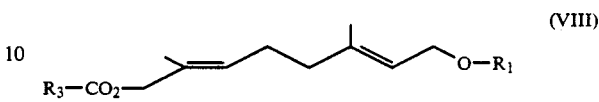

(VIII)

wherein $R_3$ is a suitable group, e.g. lower alkyl or phenyl, by reacting said allylchloride with a suitable salt of $C_1$-$C_4$ carboxylic acid such as sodium formate, sodium acetate and the like, in the presence of a suitable catalyst, viz. an iodide, e.g. a quaternary ammonium iodide, and in an inert organic solvent, e.g. a hydrocarbon such as toluene. This reaction proceeds smoothly and yields the desired ester in high yields, e.g. of up to 100%. The ester thus obtained can easily be saponified, yielding the alcohol compound of the above general formula V, wherein R is $R_1$. In fact each saponification agent can be used, such as sodium carbonate in methanol, aqueous sodium hydroxide solution and the like, in a variety of solvents, to produce the desired alcohol compound in a quantitative or substantially quantitative yield. The alcohol compound of the general formula V thus obtained thereupon can be oxidized, equally in a high yield, to the aldehyde compound of the general formula IV, wherein R is $R_1$, with air oxygen in the presence of suitable catalysts, preferably a cuprous compound and an N-oxy compound, in a polar organic solvent, preferably a dipolar organic solvent such as dimethylformamide.

As an additional aspect of the invention it has been found, that the format of the intermediate ester of the above general formula VIII is even not necessary, but that the allylchloride can be converted directly, so in one reaction step, to the desired alcohol of the general formula V. This one step conversion is carried out under the influence of a suitable basic substance, viz. an alkali metal carbonate or bicarbonate, e.g. sodium carbonate or sodium hydrogen carbonate, in a water-containing organic solvent, e.g. water-containing tetrahydrofuran, in the presence of a suitable catalyst, viz. an iodide, e.g. a quaternary ammonium iodide.

The invention will now be described in greater detail with reference to the following specific examples. In the examples the following abbreviations are used:

| | |
|---|---|
| dimethyl-tert. butylsilyl = | DMBSi |
| dimethyl-1,1,2-trimethylpropylsilyl = | DMTSi |
| tert. butyl = | t.Bu |
| tetrahydropyran-2-yl = | THP. |

EXAMPLE I

Preparation of allylchlorides from geraniol

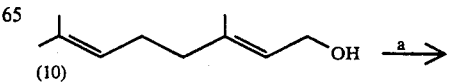

-continued

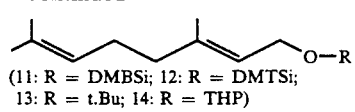

(11: R = DMBSi; 12: R = DMTSi;
13: R = t.Bu; 14: R = THP)

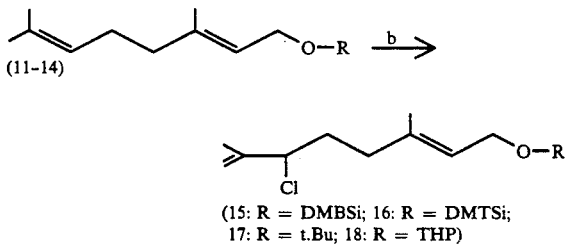

(15: R = DMBSi; 16: R = DMTSi;
17: R = t.Bu; 18: R = THP)

(a). To a solution of 30 ml (0.171 mol) of geraniol (10) in 150 ml dichloromethane, to which 0.83 g dimethylaminopyridine and 28.4 ml (0.205 mol) triethylamine have been added, is added dropwise at approx. 25° C. a solution of 28.4 g dimethyl-tert. butylsilylchloride in 50 ml dichloromethane. Stirring overnight at room temperature under nitrogen. After addition of 130 ml dichloromethane and 130 ml water, the phases are separated, after which the organic layer is washed with conc. NH$_4$Cl-solution and dried. Evaporation of the solvent in vacuo yields 46,84 g of an oily product, which is chromatographically purified over silica by elution with hexane/ethyl acetate 9/1. After evaporation to dryness the desired product (11) is obtained in a yield of 43.60 g (95%).

Purity according to G.C.: 99.6%. Identification by NMR: $^1$H-NMR (CDCl$_3$); δ: 5.24 (t.1H); 5.03 (t.1H); 4.14 (d.2H); 1.9–2.1(4H); 1.61(s.3H); 1.55(s.3H); 1.53(s.3H); 0.84(s.9H); 0.07(s.6H).

In a corresponding manner compound (12) is prepared, starting from geraniol and dimethyl-1,1,2-trimethylpropylsilylchloride; yield 87%. The compound is identified by NMR: $^1$H-NMR (CDCl$_3$); δ: 5.31 (t.1H)1; 5.09 (t.1H); 4.17 (d.2H); 2.09 (m.2H); 2.01 (m.2H); 1.67 (d.3H); 1.61 (s.3H); 1.59 (s.3H); 1.75–1.55 (1H); 0.89 (d.6H); 0.85 (s.6H); 0.1 (s.-6H).

Compound (13) is prepared as follows: To a solution of 18.9 g t.butyltrichloroacetimidate in 50 ml cyclohexane is added a solution of 12.1 g geraniol (10) in 50 ml cyclohexane. After external cooling in ice is added dropwise in 15 min 0.8 ml BF$_3$-etherate. The reaction mixture is stirred at room temperature for 2 hours. Then 1.0 g NaHCO$_3$ is added and the mixture is stirred for 10 min. The precipitate is filtered off and washed with hexane. After separation, washing with 5% aqueous NaHCO$_3$-solution and water successively, drying and evaporation to dryness, the organic phase yields 17.3 g of a product. This product is purified by flash chromatography; the desired t.butylether (13) is obtained in a yield of 11.43 g (69%). Identification by NMR: $^1$H-NMR(CDCl$_3$); δ: 5.33 (t.1H); 5.09 (t.1H); 3.92 (d.2H); 2.15–1.95 (4H); 1.67 (s.3H); 1.66(s.-3H); 1.59 (s.3H); 1.23 (s.9H).

Compound (14) is prepared exactly as described by Cardillo in Synthesis 1979, 618, from geraniol (10), dihydropyran in hexane as a solvent in the presence of Amberlyst H15 ®. Yield 77%. Identification by $^1$H-NMR.

(b) The geranylether (11), obtained as described in Example I (a), is dissolved in a quantity of 100 g in 500 ml dichloromethane. To this solution is added 426 ml of an aqueous 7.8%-NaOCl solution (0.447 mol). To this mixture, cooled down to approx. 0° C., is added 24.3 ml (0.425 mol) acetic acid in 24.3 ml water. After stirring for 0.5 hr at 0° C. the reaction is complete (GC) and the reaction mixture is allowed to reach room temp. The layers are separated, the water layer is washed with dichloromethane and the combined organic layers are washed with water, dried and evaporated to dryness. The desired allylchloride (15) is obtained in a yield of 105.39 g (93.3%) Identification by NMR: $^1$H-NMR (CDCl$_3$); δ: 5.36 (t.1H); 5.03 (s.1H); 4.92 (s.1H); 4.38 (t.1H); 4.21 (d.2H); 2.2–1.9 (m.4H); 1.83 (s.3H); 1.65 (s.3H); 0,93 (s.9H); 0.10 (s.6H).

In a corresponding manner, in which, if desired, 1N hydrochloric acid instead of acetic acid-water is used, compounds (16), (17) and (18) are prepared. Identification by NMR: Compound (16): $^1$H-NMR (CDCl$_3$); δ: 5.34 (t.1H); 4.99 (m.1H); 4.88 (m.1H); 4.34 (t.1H); 4.16 (d.2H); 2.2–1.83 (4H); 1.80 (s.3H); 1.73–1.55 (1H); 1.62 (s.3H); 0.89 (d.6H); 0.85 (s.6H); 0.1 (s.6H).

Compound (17): $^1$H-NMR (CDCl$_3$); δ: 5.35 (t.1H); 5.00 (s.1H); 4.89 (s.1H); 4.35 (t.1H); 3.92 (d.2H); 2.2–1.8 (4H); 1.80 (s.3H); 1.66 (s.3H); 1.23 (s.9H).

Compound (18): $^1$H-NMR (CDCl$_3$); δ: 5.40 (t.1H); 5.00 (m.1H); 4.89 (m.1H); 4.63 (s t.1H); 4.35 (t.1H); 4.23 (dd.1H); 4.03 (dd.1H); 3.88 (m.1H); 3.52 (m.1H); 2.3–1.4(10H); 1.81 (d.3H); 1.68 (s.3H).

(c) The geranylether (11), obtained as described in Example I (a), can alternatively be converted to the desired allylchloride as follows. Said geranylether in a quantity of 2.0 g is dissolved in 20 ml ethylacetate. Trichloroisocyanuric acid in a quantity of 0.68 g is added to this solution under nitrogen and while cooling externally at −30° C. Thereupon 10 ml 5% NaHCO$_3$-solution in water are added.

The layers are separated and the organic layer is washed successively with 5% NaHCO$_3$-solution and twice with water. After drying and evaporation to dryness in vacuo, the desired allylchloride (15) is obtained in a yield of 2.07 g.

EXAMPLE II

Preparation of alcohol compounds from allylchlorides.

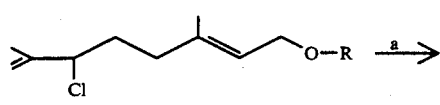

(15–18)

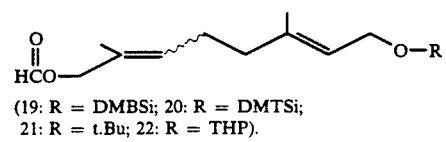

(19: R = DMBSi; 20: R = DMTSi;
21: R = t.Bu; 22: R = THP).

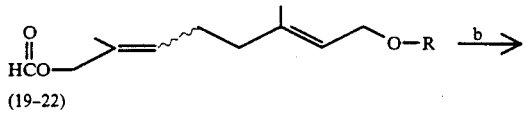

(19–22)

-continued

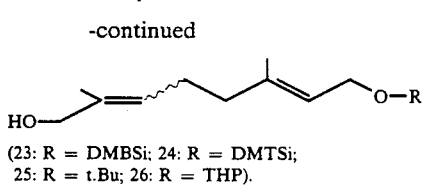

(23: R = DMBSi; 24: R = DMTSi;
25: R = t.Bu; 26: R = THP).

(a) To a solution of 2.0 g allylchloride (15) in 10 ml toluene are added while stirring 0.63 g sodium formate and 0.12 g tetrabutylammoniumiodide. Reflux overnight. The formed formate (19) is not isolated but directly converted to the alcohol compound (23). The formation of intermediate formate (19) is demonstrated by taking a sample and analysis by NMR : $^1$H-NMR (CDCl$_3$); δ: 8.09 (s.1H); 5.49–5.41–5.31 (3t.2H); 4.67–4.54 (2s.2H); 4.19 (d.2H); 2.19 (m.2H); 2.04 (m.2H); 1.76–1.67–1.63–1.62 (4s.6H); 0.90 (s.9H); 0.07 (s.6H). The ratio of E : Z in the E/Z mixture is 60:40.

In a corresponding manner compounds (20), (21) and (22) are prepared.
Identification by NMR:

Compound (20): $^1$H-NMR (CDCl$_3$); δ: 8.08 (s.1H); 5,49–5.41 (2t.1H); 5.31 (t.1H); 4.67–4.53 (2s.2H), 4.17 (d.2H); 2.19 (m.2H); 2.04 (m.2H); 1.7–1.55 (m.1H); 1.75–1.67 (2s.3H); 1.62–1.61 (2s.3H); 0.89 (d.6H); 0.85 (s.6H); 0.12 (s.6H). E/Z ratio 60:40.

Compound (21) $^1$H-NMR (CDCl$_3$); δ: 8.11 (s.1H); 5.49–5.42–5.33 (3t.2H); 4.67–4.55 (2s.2H); 3.92 (d.2H); 2.20 (m.2H); 2.05 (m.2H); 1.76–1.66 (2m.6H); 1.23 (s.9H). E/Z ratio 50:50

Compound (22): $^1$H-NMR (CDCl$_3$); δ:8.09 (s.1H); 5.49–5.41 (2t.1H); 5.37 (t.1H); 4.67–4.54 (2s.2H); 4.62 (t.1H); 4.23 (dd.1H); 4.02 (dd.1H); 3.88 (m.1H); 3.51 (m.1H); 2.3–2.0 (4H); 1.9–1.4 (6H); 1.76 (d.3H); 1.67 (2s.3H). E/Z ratio 50:50.

(b) The formate (19) is converted to alcohol compound (23) by adding to the solution, obtained according to Example II(a), a solution of 317 mg NaOH in a mixture of 0.32 ml water and 6.14 ml methanol. Stirring at room temp. for 0.5 hr. After addition of 20 ml water the layers are separated and the water layer extracted with toluene. The combined organic layers are washed with water, dried and evaporated to dryness, yielding the desired alcohol compound (23) in 1.64 g (overall yield 87.4 %). Identification by NMR: $^1$H-NMR (CDCl$_3$); δ: 5.39–5.28 (tm.2H); 4.18 (dd.2H); 4.07–3.97 (2s.2H); 2.16 (m.2H); 2.03 (m.2H); 1.96 (s.1H); 1.78–1.65 (ds.3H); 1.63 (s.3H); 0.91 (s.9H); 0.08 (s.6H).

The ratio of E:Z in the E/Z mixture in 56:44.

In a corresponding manner, in which, if desired, sodium carbonate in methanol is used for the saponification, compounds (24), (25) and (26) are prepared in overall yield of 7%, 100% and 53%, respectively. Identification by NMR:

Compound (24): $^1$H-NMR (CDCl$_3$); δ: 5.42–5.18 (t,m.2H); 4.16 (2d.2H); 4.07–3.95 (2s.2H); 2.35 (s.1H); 2.16 (m.2H); 2.03 (m.2H); 1.8–1.75 (3s,m.7H); 0.89 (d.6H); 0.85 (s.6H); 0.10 (s.6H). E/Z ratio 60:40.

Compound (25): $^1$H-NMR (CDCl$_3$); δ: 5.42–5.14 (tmt.2H); 4.01–3.96–3.82 (sm.4H); 3.11 (s.1H); 2.22–1.95 (2m.4H); 1.77–1.65–1.63 (3s.6H); 1.22 (s.9H). E/Z ratio 50:50.

Compound (26): $^1$H-NMR (CDCl$_3$); δ:5.37 (t.1H); 5.33–5.22 (2t.1H); 4.63 (t.1H); 4.21 (m.1H); 4.06–3.94 (2s.2H); 4.01 (m.1H); 3.87 (m.1H); 3.50 (m.1H); 3.08–2.97 (2s.1H); 2.25–2.0 (4H); 1.9–1..4 (6H); 1.78–1.-68–1.65 (3s.6H). E/Z ratio 50:50.

EXAMPLE III

Preparation of alcohol compound (23) from allylchloride (15)

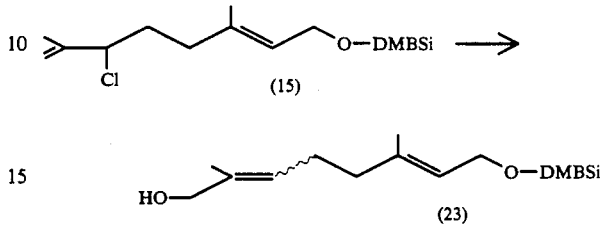

To a solution of 1.0 g allylchloride (15) in 5 ml tetrahydrofuran are successively added 1.32 g Na$_2$CO$_3$·10 aq and 0.244 g tetrabutylammonium iodide. The reaction mixture is refluxed for some days and then subjected to a work-up procedure by adding 10 ml toluene and 10 ml water. The phases are separated and the toluene layer is washed twice with 10 ml water and evaporated to dryness. The desired alcohol compound (23) is obtained in a yield of 0.67 g (75%). The NMR-spectrum corresponds with that of compound (23) prepared according to Example II.

EXAMPLE IV

Oxidation of alcohol compounds to aldehyde compounds.

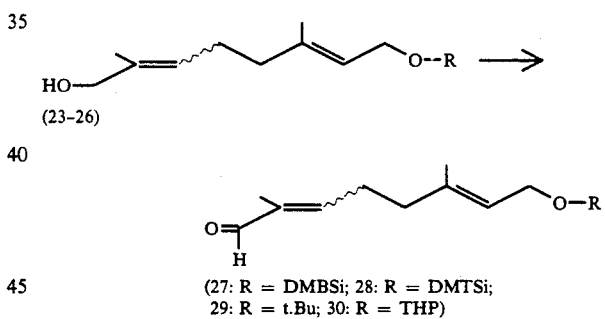

(27: R = DMBSi; 28: R = DMTSi;
29: R = t.Bu; 30: R = THP)

The alcohol compound (23), obtained as described in Example II (b), is converted into the corresponding aldehyde by dissolving 4.63 g thereof in 23.2 ml dimethylformamide. To this solution are added 255 mg 2,2,6,6-tetramethylpiperidine-N-oxide and 161 mg of cuprochloride. The reaction mixture is flushed with air and heated to 35°–40° C. while stirring. After 5.5 hours the reaction mixture is cooled down to room temperature; 77 ml of diethylether and a mixture of 25 ml water and 15 ml 2N hydrochloric acid are added. After separation of the layers, the water layer is extracted with diethylether. The combined ether layers are washed with water, dried and evaporated to dryness. The desired aldehyde compound (27) is obtained in a yield of 4.25 g (92.5%). The product is identified by NMR: $^1$H-NMR (CDCl$_3$); δ: 10.13–9.38 (2s.1H); 6.48 (m.1H); 5.35 (m.1H); 4.20 (m.2H); 2.70–2.49 (2m.2H); 2.18 (m.2H); 1.77–1.75 (2s.3H); 1.66–1.64 (2s.3H); 0.91 (s.9H); 0.07 (s.6H).

In a corresponding manner the aldehyde compounds (28), (29) and (30) are prepared from the corresponding alcohol compounds in yields of 98%, 77% and 89% respectively. Identification by NMR:

Compound (28): $^1$H-NMR (CDCl$_3$); δ: 9.38 (s.1H); 6,47 (t.1H); 5.35 (t.1H); 4.18 (d.2H); 2.49 (m.2H); 2.19 (m.2H); 1.75 (s.3H); 1.65 (s.3H); 1.62 (m.1H); 0.88 (d.6H); 0.85 (s.6H): 0.10 (s.6H).

Compound (29): $^1$H-NMR (CDCl$_3$); δ: 9.40 (s.1H); 6.48 (t.1H); 5.37 (t.1H); 3.93 (d.2H); 2.50 (m.2H); 2.21 (m.2H); 1.76 (s.3H); 1.69 (s.3H); 1.23 (s.9H).

Compound (30): $^1$H-NMR (CDCl$_3$); δ: 9.40 (s.1H); 6.48 (t.1H); 5.42 (t.1H); 4.62 (m.1H); 4.25–4.04 (dd.2H); 3.88–3.51 (2m.2H); 2.52 (q.2H), 2.24 (t.2H); 1.75 (s.3H); 1.72 (s.3H); 1.90–1.50 (m.6H).

What is claimed is:

1. Use of an allychloride of the formula

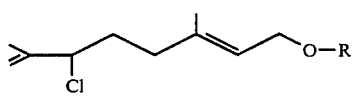
(I)

wherein

R is a C$_1$–C$_{12}$ alkyl group or a C$_2$–C$_{12}$ alkenyl group, which groups may be substituted with one or more substituents selected from the group consisting of C$_1$–C$_4$ alkoxy, halogen, unsubstituted phenyl and substituted phenyl; a (trihydrocarbyl)silyl group; a (dihydrocarbyl)(hydrocarbyloxy)silyl group; or a dihydropyran-2-yl group, a tetrahydropyran-2-yl group, a dihydrofur-2-yl group or a tetrahydrofur-2-yl group, which groups may be substituted with C$_1$–C$_6$ alkyl;

for preparing an aldehyde compound of the formula

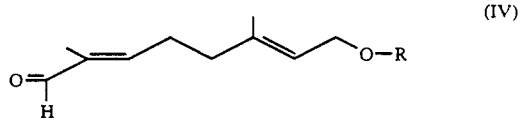
(IV)

wherein R has the above meaning, by successively:
 (i) converting said allylchloride with a salt of a C$_1$–C$_4$ carboxylic acid, in the presence of an iodide as a catalyst, and in an inert organic solvent, at increased temperature, followed by saponification of the ester thus obtained into an alcohol compound of the formula

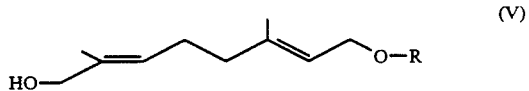
(V)

and
 (ii) oxidizing the alcohol compound thus obtained with oxygen in the presence of a cuprous compound and an N-oxy compound as catalysts, in a dipolar organic solvent.

2. Use of an allylchloride as claimed in claim 1, said allylchloride having the formula

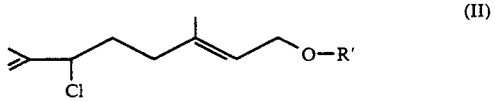
(II)

wherein R' is a tert.(C$_4$–C$_{12}$)alkyl group, a tetrahydropyran-2-yl group, a tetrahydrofur-2-yl group, an ethoxyethyl group, or a tri(hydrocarbyl)silyl group wherein hydrocarbyl is selected from the group consisting of C$_1$–C$_8$ alkyl and phenyl.

3. Use of an allylchloride for preparing an aldehyde as claimed in claim 1, wherein said conversion into an alcohol compound of the formula V, presented in claim 1, is carried out under the influence of a basic substance, selected from an alkali metal carbonate or bicarbonate, in a water-containing organic solvent and in the presence of an iodide as a catalyst and at increased temperature.

* * * * *